(12) United States Patent
Seubert et al.

(10) Patent No.: US 8,445,264 B2
(45) Date of Patent: May 21, 2013

(54) SYSTEMS AND METHODS FOR HARVESTING TARGET PARTICLES OF A SUSPENSION

(75) Inventors: Ronald C. Seubert, Sammamish, WA (US); Paul C. Goodwin, Shoreline, WA (US); Jackie L. Stillwell, Sammamish, WA (US)

(73) Assignee: Rarecyte, Inc., Seattle, WA (US)

( * ) Notice: Subject to any disclaimer, the term of this patent is extended or adjusted under 35 U.S.C. 154(b) by 0 days.

(21) Appl. No.: 13/372,815

(22) Filed: Feb. 14, 2012

(65) Prior Publication Data

US 2012/0258531 A1 Oct. 11, 2012

Related U.S. Application Data

(60) Provisional application No. 61/473,602, filed on Apr. 8, 2011.

(51) Int. Cl.
*C12M 1/34* (2006.01)
(52) U.S. Cl.
USPC ..... 435/287.1; 422/401; 422/405; 435/288.1; 435/810; 436/810
(58) Field of Classification Search
None
See application file for complete search history.

(56) References Cited

U.S. PATENT DOCUMENTS

| 6,197,523 | B1 * | 3/2001 | Rimm et al. | 435/7.1 |
| 7,074,577 | B2 * | 7/2006 | Haubert et al. | 435/7.24 |
| 2011/0067488 | A1 * | 3/2011 | Levine et al. | 73/61.71 |

OTHER PUBLICATIONS

Rice AP and Herrmann CH. Preparation of primary human monocytes/macrophages, Rice & Herrmann Laboratory/Protocols. http://www.bcm.edu/molvir/ricelab/index.cfm?PMID17987, last modified on Aug. 31, 2010.*

* cited by examiner

*Primary Examiner* — Jon P Weber
*Assistant Examiner* — Chunyuan Luo
(74) *Attorney, Agent, or Firm* — Olympic Patent Works PLLC

(57) ABSTRACT

Tube and float systems and methods for isolating, enumerating, and harvesting target materials of a suspension are described. In one aspect, a tube and float system includes a filter embedded in a tube cap. The filter enables the passage of fluids but prevents the passage of the target materials. The tube and float system can be used to isolate and enumerate the target materials by centrifuging the tube and float system with the suspension to trap the target materials between the float and inner wall of the tube. Fluids above and below the float are poured off and a second fluid can be introduced to the tube to re-suspend the trapped target material. The second fluid can be poured through the filter in the cap to trap the target material against the filter. The target material can be enumerated and analyzed.

15 Claims, 10 Drawing Sheets

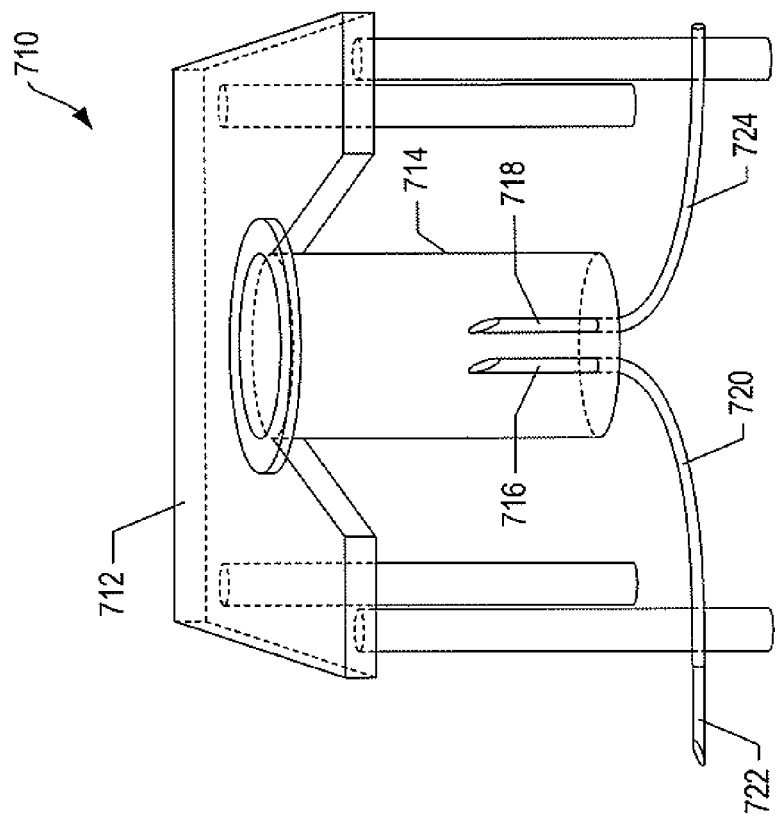
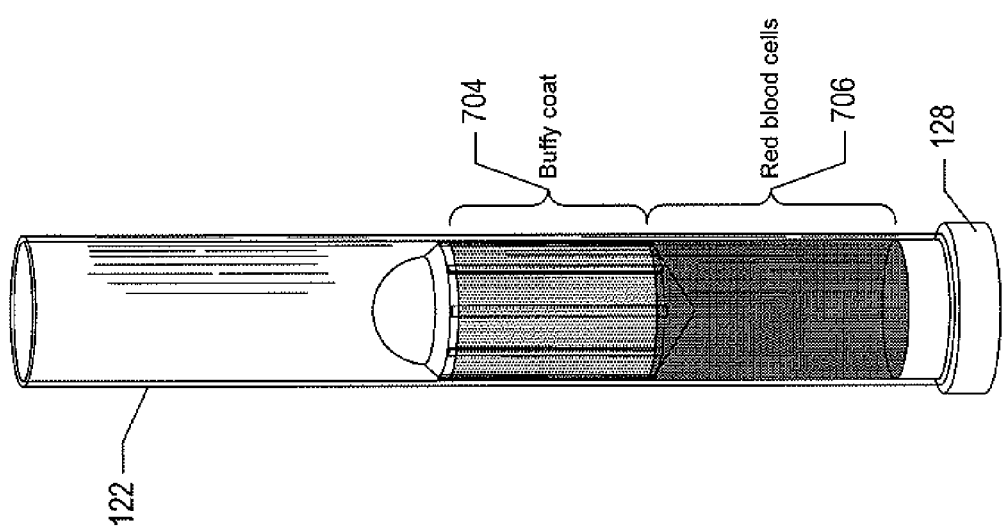
FIG. 7D
FIG. 7C

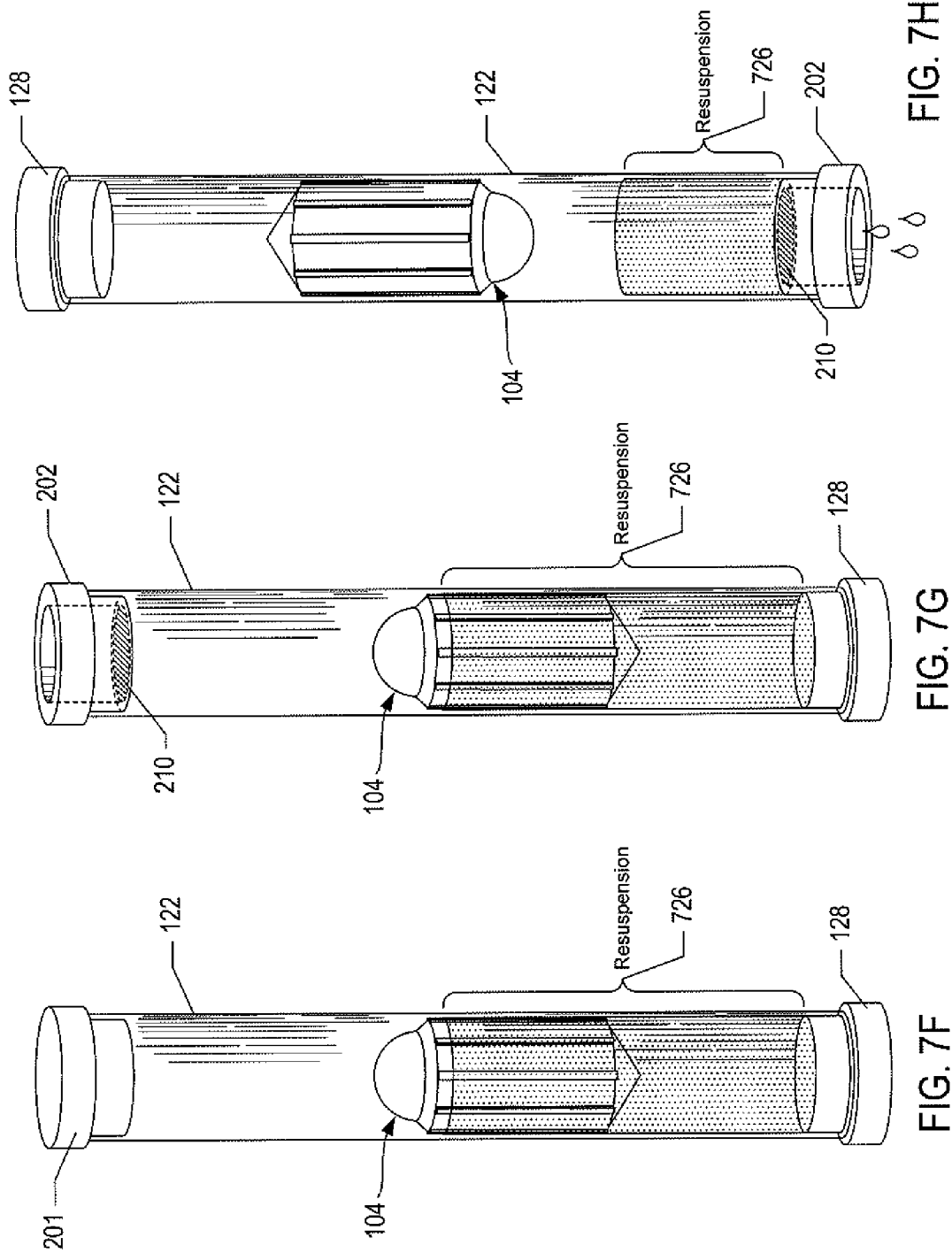

SYSTEMS AND METHODS FOR HARVESTING TARGET PARTICLES OF A SUSPENSION

CROSS-REFERENCE TO RELATED APPLICATION

This application claims the benefit of Provisional Application No. 61/473,602, filed Apr. 8, 2011.

TECHNICAL FIELD

This disclosure relates to capturing and isolating target materials of a suspension.

BACKGROUND

Suspensions often include particles of interests that are difficult to extract and isolate for analysis because the particles occur with such low frequency. For example, blood is a suspension of various particles that is routinely examined for the presence of abnormal organisms or cells, such as circulating tumor cells ("CTCs"), fetal cells or ova, parasites, microorganisms, and inflammatory cells. CTCs are of particular interest because CTCs are cancer cells that have detached from a primary tumor, circulate in the bloodstream, and may be regarded as seeds for subsequent growth of additional tumors (i.e., metastasis) in different tissues. As a result, detecting, enumerating, and characterizing CTCs may provide valuable information in monitoring and treating cancer patients. Although detecting CTCs may help clinicians and cancer researchers predict a patient's chances of survival and/or monitor a patient's response to cancer therapy, CTC numbers are typically very small and are not easily detected. In particular, typical CTCs are found in frequencies on the order of 1-10 CTCs per milliliter sample of whole blood obtained from patients with a metastatic disease. By contrast, a single milliliter sample of whole blood typically contains a few million white blood cells and 4-6 billion red blood cells. In addition to detecting, enumerating, and characterizing CTCs in formulating a therapeutic cancer treatment, it may also be valuable to have additional CTC information such as nucleic acid or proteomic signatures. For example, a CTC distribution and potentially even the CTC itself may vary over time after cancer therapy begins. However, in order to obtain this additional information, the CTCs have to be harvested from a whole blood sample and analyzed with molecular techniques.

Practitioners, researchers, and those working with suspensions continue to seek systems and methods for detecting, enumerating, characterizing, and harvesting various kinds of particles found in a suspension.

SUMMARY

Tube and float systems and methods for isolating and enumerating target materials of a suspension are disclosed. A suspension suspected of containing a target material is added to the tube. The float is also added to the tube, and the tube, float, and suspension are centrifuged together, causing the various materials suspended in the suspension to separate into different layers along the axial length of the tube according to their specific gravities. The float has a specific gravity that positions the float at approximately the same level as the layer expected to contain the target material when the tube, float and suspension are centrifuged together. During centrifugation, the float is positioned in and expands the axial length of the layer containing the target material so that nearly the entire quantity of target material is positioned between the float outer surface and the inner surface of the tube, enabling all or nearly all of the target material contained in the suspension to be detected, imaged, enumerated, harvested, and even identified based on appropriate molecular markers attached to the target material. The tube and float systems include a separation filter embedded in the tube cap. The filter enables the passage of fluids but prevents the passage of the target material. In particular, fluids located above and below the float are removed after centrifugation. A second fluid can be introduced to the tube to re-suspend the target material trapped between the float outer surface and the inner surface of the tube. The second fluid can be poured through the filter in order to trap the target material against the filter, enabling enumeration and analysis of the target material.

BRIEF DESCRIPTION OF THE DRAWINGS

FIGS. 7A-7H show a method for extracting circulating tumor cells from a whole blood sample.

DETAILED DESCRIPTION

Systems and methods for separating, enumerating, harvesting, and isolating target materials of a suspension for analysis are now described. A suspension is a fluid containing particles that are sufficiently large for sedimentation. Examples of suspensions include paint, urine, anticoagulated whole blood, and other bodily fluids. A target material can be cells, organisms, or particles whose density equilibrates when the suspension is centrifuged. Examples of target materials found in suspensions obtained from living organisms include cancer cells, ova, inflammatory cells, viruses, parasites, and microorganisms, each of which has an associated specific gravity. The detailed description is organized into two subsections as follows: Various tube and float systems for isolating and separating target materials from other materials in a suspension are described below in a first subsection. Methods for separating the target materials for analysis using tube and float systems are described in a second subsection.

Tube and Float Systems

Figure 1A:
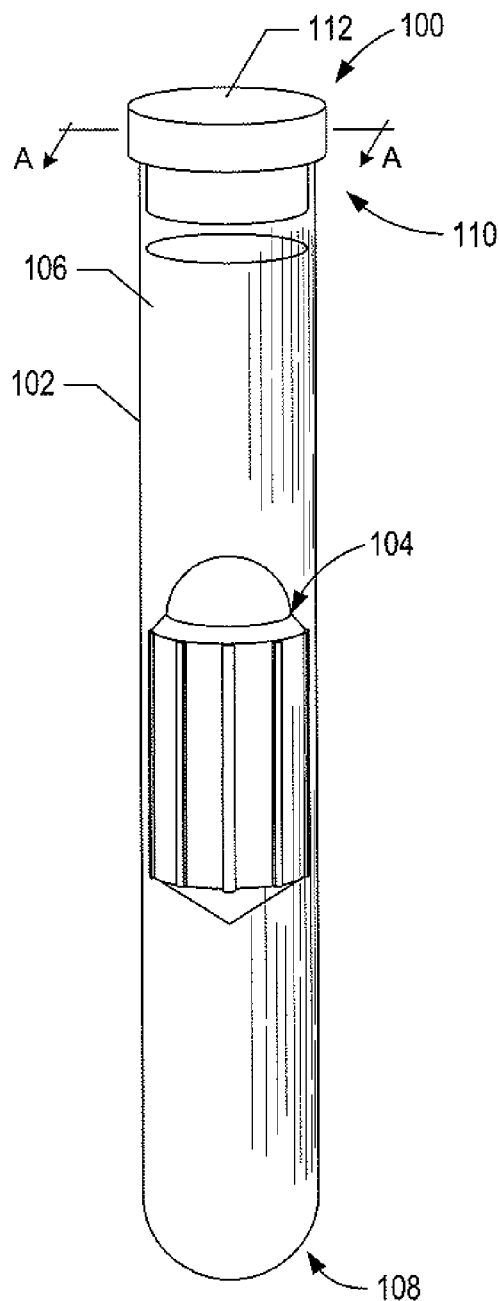
FIGS. 1A-1B show isometric views of two example tube and float systems.
Figure 1B:
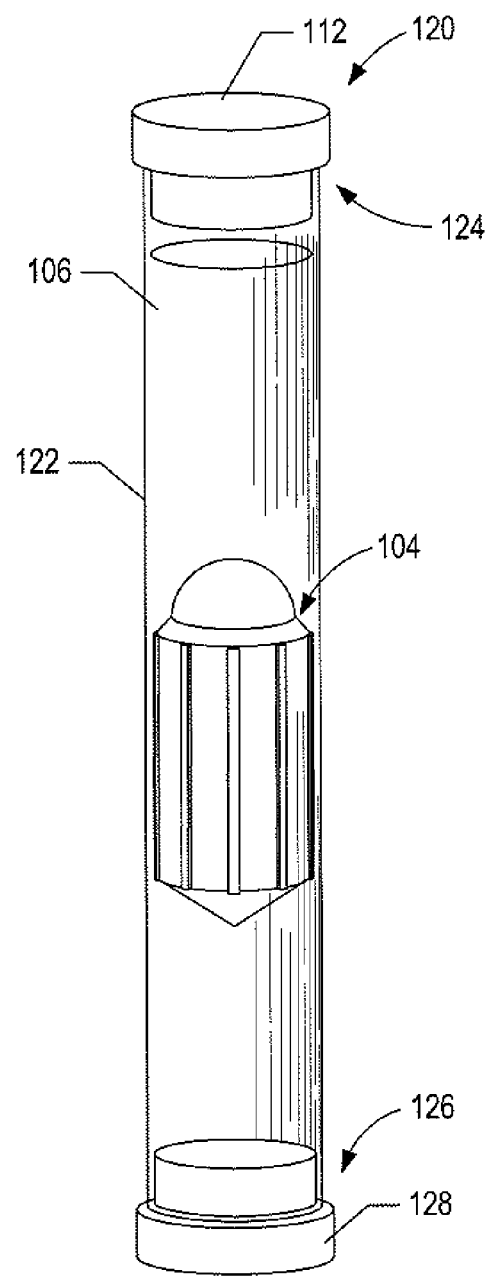

FIG. 1A shows an isometric view of an example tube and float system 100. The system 100 includes a tube 102 and a float 104 suspended within a suspension 106. In the example of FIG. 1A, the tube 102 has a circular cross-section, a first closed end 108, and a second open end 110. The open end 110 is sized to receive a stopper or cap 112. The tube may also have two open ends that are sized to receive stoppers or caps, such as the example tube and float system 120 shown FIG. 1B. The system 120 is similar to the system 100 except the tube 102 is replaced by a tube 122 that includes two open ends 124 and 126 configured to receive the cap 112 and a cap 128, respectively. The tubes 102 and 122 have a generally cylindrical geometry, but may also have a tapered geometry that widens toward the open ends 110 and 124, respectively. Although the tubes 102 and 122 have a circular cross-section, in other embodiments, the tubes 102 and 122 can have elliptical, square, triangular, rectangular, octagonal, or any other suitable cross-sectional shape that substantially extends the length of the tube. The tubes 102 and 122 can be composed of a transparent or semitransparent flexible material, such as flexible plastic or another suitable material.

Figure 2:
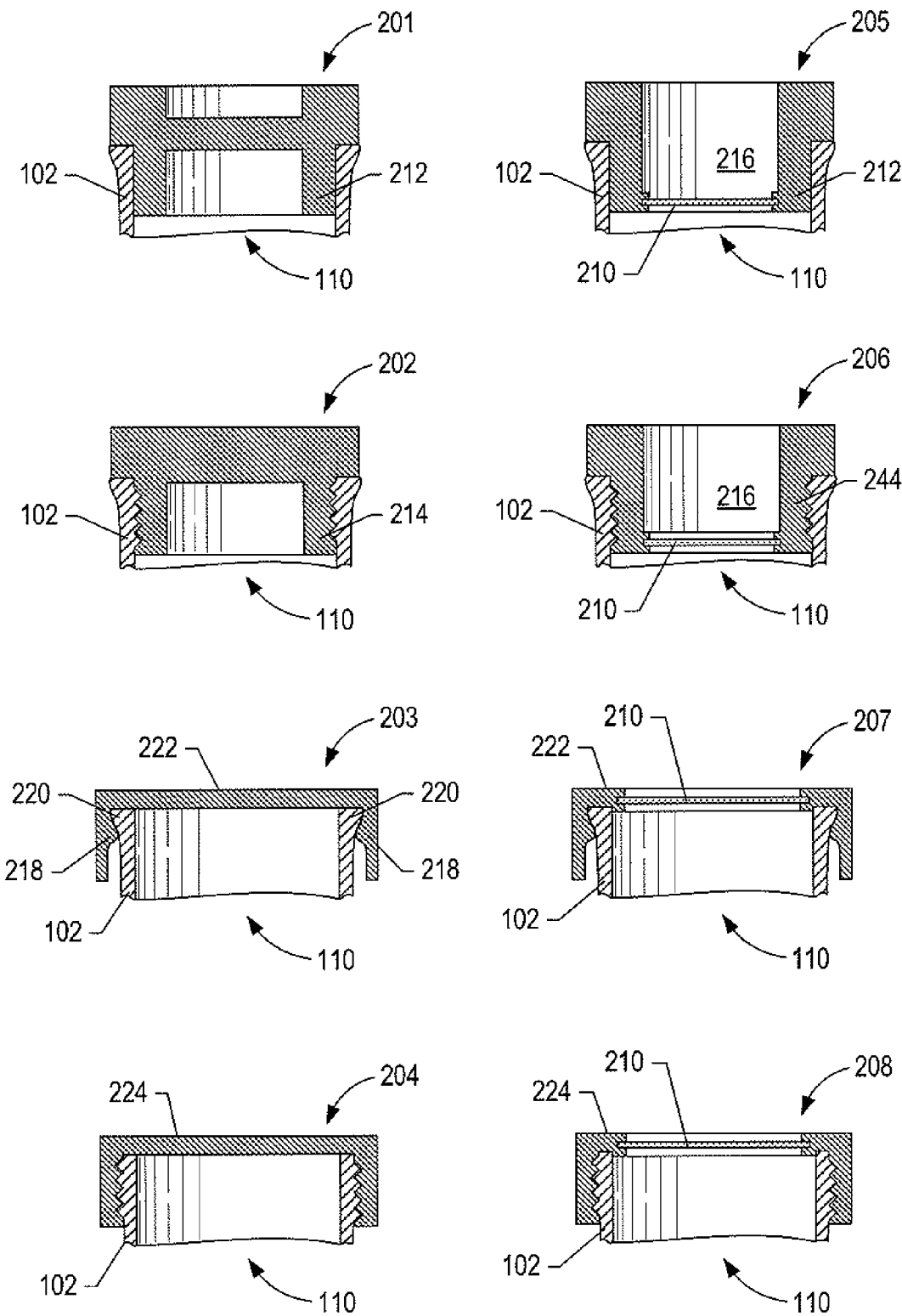
FIG. 2 shows cross-sectional views, along a line A-A shown in FIG. 1, of eight different examples of caps that can be attached to the open end of a tube of a tube and float system.

FIG. 2 shows cross-sectional views, along a line A-A shown in FIG. 1, of eight different examples of caps 112 that can be attached to the open end 110 of the tube 102. Caps 201-204 represent four different kinds of cap embodiments for sealing the open end 110 of the tube 102. Caps 205-208 each include a filter 210 composed of a porous material that allows the passage of fluids and prevents the passage of particles larger than the diameter of the filter 210 pores. The filter 210 is used, as described below, to separate the target material from other suspension materials and fluids contained within the tube 102. Caps 201 and 205 include a hollow bottom plug 212 with a diameter larger than the diameter of the open end 110. The caps 201 and 205 are held in place by frictional forces that effectively seal the open end 110 of the tube 102 by preventing fluids from seeping between the outer surface of the plug 212 and the inner wall of the tube 102. Caps 202 and 206 include a threaded plug 214. The inner wall of the open end 110 is also threaded to receive the threaded plug 214 and form a seal that effectively prevents fluids from seeping between the outer surface of the plug 214 and the inner wall of the tube 102. In the examples of FIG. 2, the filters 210 of caps 205 and 206 are located near the base of the plugs 212 and 214. In other embodiments, the filters 210 can located anywhere along the openings 216 of the caps 205 and 206. Cap 203 includes an inner raised ring 218 with a smaller diameter than a raised outer ring 220 of the tube 102. The cap 203 can be a thumb cap that is snapped into place over the open end 110, holding the lid 222 firmly against the open end 110 and effectively closing the tube 102. Cap 207 can also be a thumb cap similar to the cap 203 except the filter 210 is embedded in the lid 222. Cap 204 and the outer surface of tube 102 near the open end 110 of the tube 102 are threaded. The cap 204 is screwed into place, which holds the lid 224 firmly against the open end 110 effectively closing the tube 102. Cap 208 is similar to the cap 204 except the filter 210 is embedded in the lid 224. The caps can be composed of a plastic, such as polypropolyne, polyethylene, rubber, or another suitable material.

Figure 3:
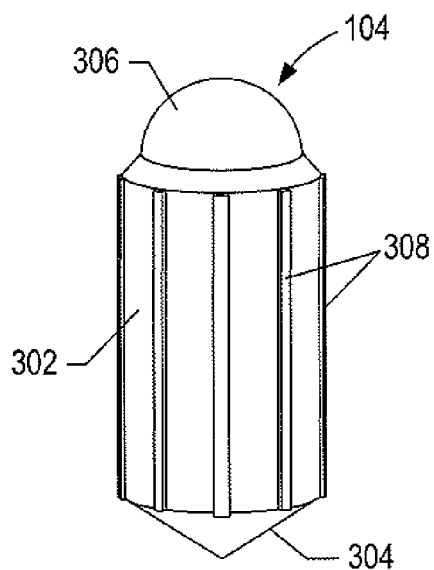
FIG. 3 shows an isometric view of the example float of the tube and float system shown in FIG. 1.

FIG. 3 shows an isometric view of the float 104 shown in FIG. 1. The float 104 includes a main body 302, a cone-shaped tapered end 304, a dome-shaped end 306, and splines 308 radially spaced and axially oriented on the main body 302. The splines 308 provide a sealing engagement with the inner wall of the tube 102. In alternative embodiments, the number of splines, spline spacing, and spline thickness can each be independently varied. The splines 308 can also be broken or segmented. The main body 302 is sized to have an outer diameter that is less than the inner diameter of the tube 102, thereby defining fluid retention channels between the outer surface of the body 302 and the inner wall of the tube 102. The surfaces of the main body 302 between the splines 308 can be flat, curved or have another suitable geometry. In the example of FIG. 3, the splines 308 and the main body 302 form a single structure.

Figure 4:
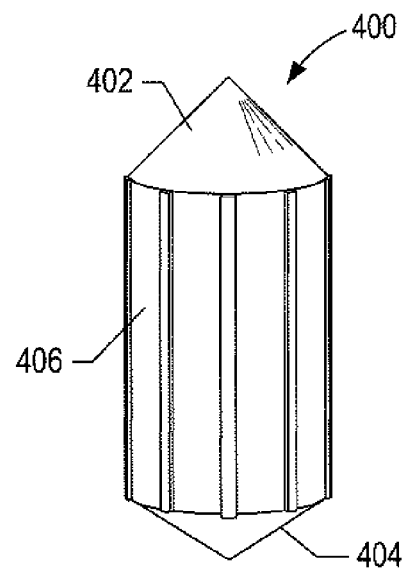
FIGS. 4-6 show examples of different types of floats.

Embodiments include other types of geometric shapes for float end caps. FIG. 4 shows an isometric view of an example float 400 with two cone-shaped end caps 402 and 404. The main body 406 of the float 400 includes the same structural elements (i.e., splines and bore holes) as the float 104. A float can also include two dome-shaped end caps. The float end caps can include other geometric shapes and are not intended to be limited the shapes described herein.

Figure 5:
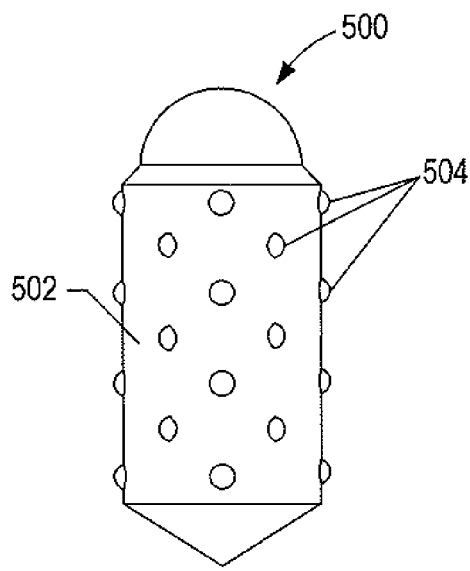
Figure 6:
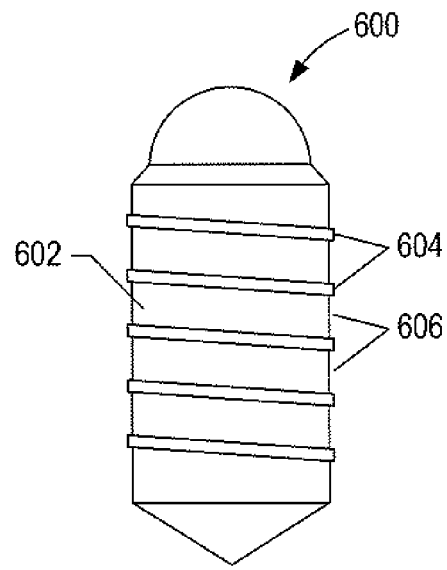

In other embodiments, the main body of the float 104 can include a variety of different support structures for separating target materials, supporting the tube wall, or directing the suspension fluid around the float during centrifugation. FIGS. 5-6 show examples of two different types of main body structural elements. Embodiments are not intended to be limited to these two examples. In FIG. 5, the main body 502 of a float 500 is similar to the float 104 except the main body 502 includes a number of protrusions 504 that provide support for the deformable tube. In alternative embodiments, the number and pattern of protrusions can be varied. In FIG. 6, the main body 602 of a float 600 includes a single continuous helical structure or ridge 604 that spirals around the main body 602 creating a helical channel 606. In other embodiments, the helical ridge 604 can be rounded or broken or segmented to allow fluid to flow between adjacent turns of the helical ridge 604. In various embodiments, the helical ridge spacing and rib thickness can be independently varied.

The float can be composed of a variety of different materials including, but are not limited to, rigid organic or inorganic materials, and rigid plastic materials, such as polyoxymethylene ("Delrin®"), polystyrene, acrylonitrile butadiene styrene ("ABS") copolymers, aromatic polycarbonates, aromatic polyesters, carboxymethylcellulose, ethyl cellulose, ethylene vinyl acetate copolymers, nylon, polyacetals, polyacetates, polyacrylonitrile and other nitrile resins, polyacrylonitrile-vinyl chloride copolymer, polyamides, aromatic polyamides ("aramids"), polyamide-imide, polyarylates, polyarylene oxides, polyarylene sulfides, polyarylsulfones, polybenzimidazole, polybutylene terephthalate, polycarbonates, polyester, polyester imides, polyether sulfones, polyetherimides, polyetherketones, polyetheretherketones, polyethylene terephthalate, polyimides, polymethacrylate, polyolefins (e.g., polyethylene, polypropylene), polyallomers, polyoxadiazole, polyparaxylene, polyphenylene oxides (PPO), modified PPOs, polystyrene, polysulfone, fluorine containing polymer such as polytetrafluoroethylene, polyurethane, polyvinyl acetate, polyvinyl alcohol, polyvinyl halides such as polyvinyl chloride, polyvinyl chloride-vinyl acetate copolymer, polyvinyl pyrrolidone, polyvinylidene chloride, specialty polymers, polystyrene, polycarbonate, polypropylene, acrylonitrite butadiene-styrene copolymer and others.

Methods for Enumerating and Isolating Target Materials of a Suspension

For the sake of convenience, an example method of harvesting target materials of a suspension is now described with reference to FIGS. 7A-7H. In this example, the target materials are CTCs and the suspension is anticoagulated whole blood. Note that methods described herein are not intended to be so limited in their scope of application. In practice, methods described herein can be used to enumerate, isolate and harvest nearly any kind of target materials found in any kind of suspension and are not intended to be limited to enumerating, isolating, and harvesting CTCs of a whole blood sample.

Figure 7B:
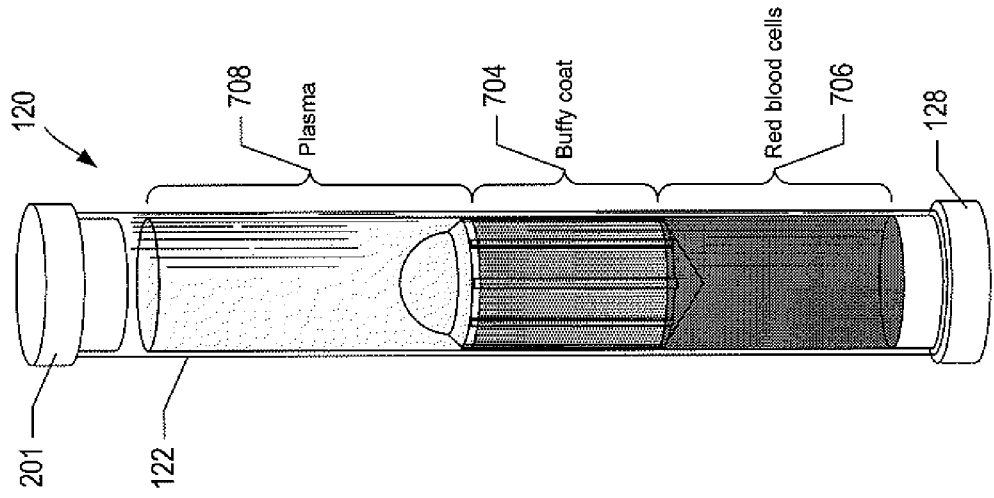
Figure 7A:
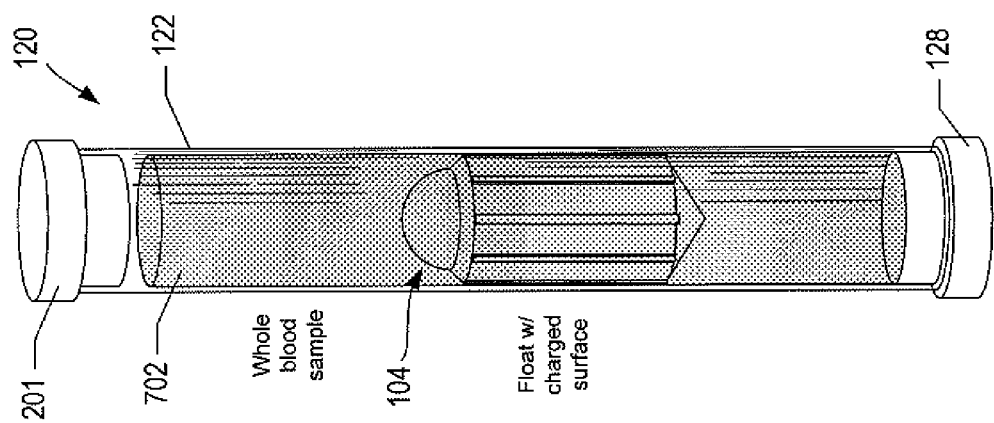

FIG. 7A shows an example of the tube and float system 120 filled with an anticoagulated whole blood sample 702. The whole blood sample 702 can be drawn into the tube 122 using venepuncture. Prior to drawing the whole blood sample into the tube 122, the float 104 is selected to have a specific gravity to position the float 104 at approximately the same level as the buffy coat. The float 104 can then be inserted into the tube 122 followed by drawing the whole blood sample 702 into the tube 122, or the float 104 can be inserted after the whole blood sample 702 has been placed in the tube 122. In the example shown in FIG. 7A, the cap 201 shown in FIG. 2 is inserted into the open end 110 of the tube 122. Any one of the caps 201-204 described above with reference to FIG. 2 can be used.

After the whole blood sample 702 is placed in the tube 122, the tube 122, the float 104, and the whole blood sample 702 are centrifuged for a period of time sufficient to separate the particles suspended in the whole blood sample 702 according to their specific gravities. FIG. 7B shows an example of the tube and float system 100 where the float 104 spreads a buffy coat 704 between a layer of packed red blood cells 706 and plasma 708. In the example of FIG. 7B, the centrifuged blood sample is composed of six layers: (1) packed red cells 706, (2) reticulocytes, (3) granulocytes, (4) lymphocytes/monocytes, (5) platelets, and (6) plasma 708. The reticulocyte, granulocyte, lymphocytes/monocyte, platelet layers form the buffy coat 704 and are the layers often analyzed to detect certain abnormalities, such as CTCs. In FIG. 7B, the float 104 expands the buffy coat, enabling the buffy coat 704 to be analyzed through the tube 122 wall. Any CTC's that lie within the buffy coat 704 fluid are located within retention channels between the float 104 outer surface and inner wall of the tube 122.

CTCs, if present, can be identified through tube 122 wall. On the one hand, when no CTCs are detected between the float 104 outer surface and the inner wall of the tube 122, or when no significant change in the number and characterization of the CTCs is detected since the last test, no further processing is required and the method can stop here. On the other hand, when CTCs are detected and enumeration, isolation, and harvesting of the CTC's is desired, the cap 201 can be removed and the plasma 708 can be poured off or aspirated with a pipette. For example, as shown in FIG. 7C, the plasma 708 is removed from the tube 122.

Next, the layer of red blood cells 706 can be removed. FIG. 7D shows a system 710 for removing the red blood cells 706. The system 710 includes a stand 712 notched to receive a translucent tube holder 714. The holder 714 has an open end dimensioned to receive the tube 122 and cap 128 and two hypodermic needles 716 and 718 located at the base of the cavity of the holder 714. The needle 716 is connected at a first end to a flexible tube 720, which is connected at a second end to a needle 722. The needle 718 is also connected to a flexible tube 724.

Figure 7E:
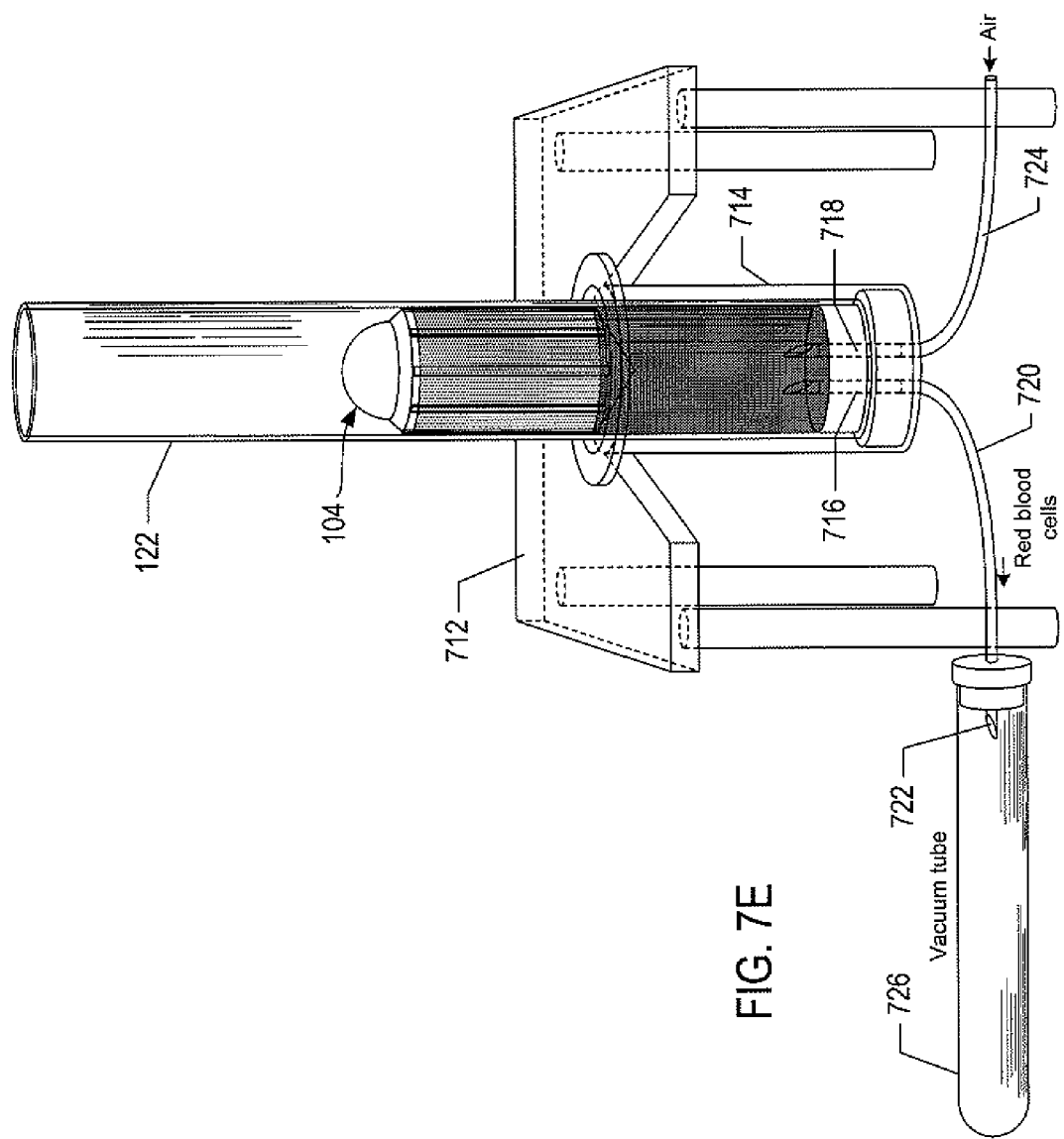

FIG. 7E shows the tube 122 and cap 128 inserted into the cavity of the holder 714 so that needles 716 and 718 puncture the cap 128. The cap 128 can be composed of rubber or include a rubber region that enables the needles to puncture cap 128 and form a liquid-tight seal around the needles 716 and 718. The needle 722 is then inserted into a vacuum tube 726. Vacuum pressure causes the red blood cells and other materials and fluids trapped below the float 104 to be sucked through the tube 720 and into the vacuum tube 726 and air is drawn through the tube 724 and into the volume of the tube 122 beneath the float 104 to release back pressure.

In alternative embodiments, because the target materials are attached to the main body of the float 104, the float 104 with protrusions can be used and the second needle 718 and tube 724 can be omitted from the system 710. The protrustions enable air to be drawn into the region beneath the float 104 via the channels between the main body of the float 104 and the inner wall of the tube 122 as the layer of red blood cells 706 is removed.

In FIG. 7F, a solution, such as a saline solution, is added to the tube 122 and the cap 201 is replaced. The tube 122, float 104, and solution are rocked or agitated for a period of time, and the CTCs in the buffy coat are re-suspended in a resuspension 726. In FIG. 7G, the cap 201 is replaced with the filter cap 202.

In FIG. 7H, the tube 122 is inverted and gravity filtering allows the resuspension fluid to pass through the filter 210 to drain off resuspended fluids trapping any CTCs against the filter 210. The tube 122 can be pneumatically coupled to a disposable container (not shown) for removal of the resuspension fluid. Once the resuspension fluid is drained off, the cap 202 can be removed and the CTCs deposited on the filter 210 can be countered or removed for molecular analysis, or the cap 202 can be washed with a saline solution to recover any CTCs trapped by the filter 210.

Figures 8A, 8B:
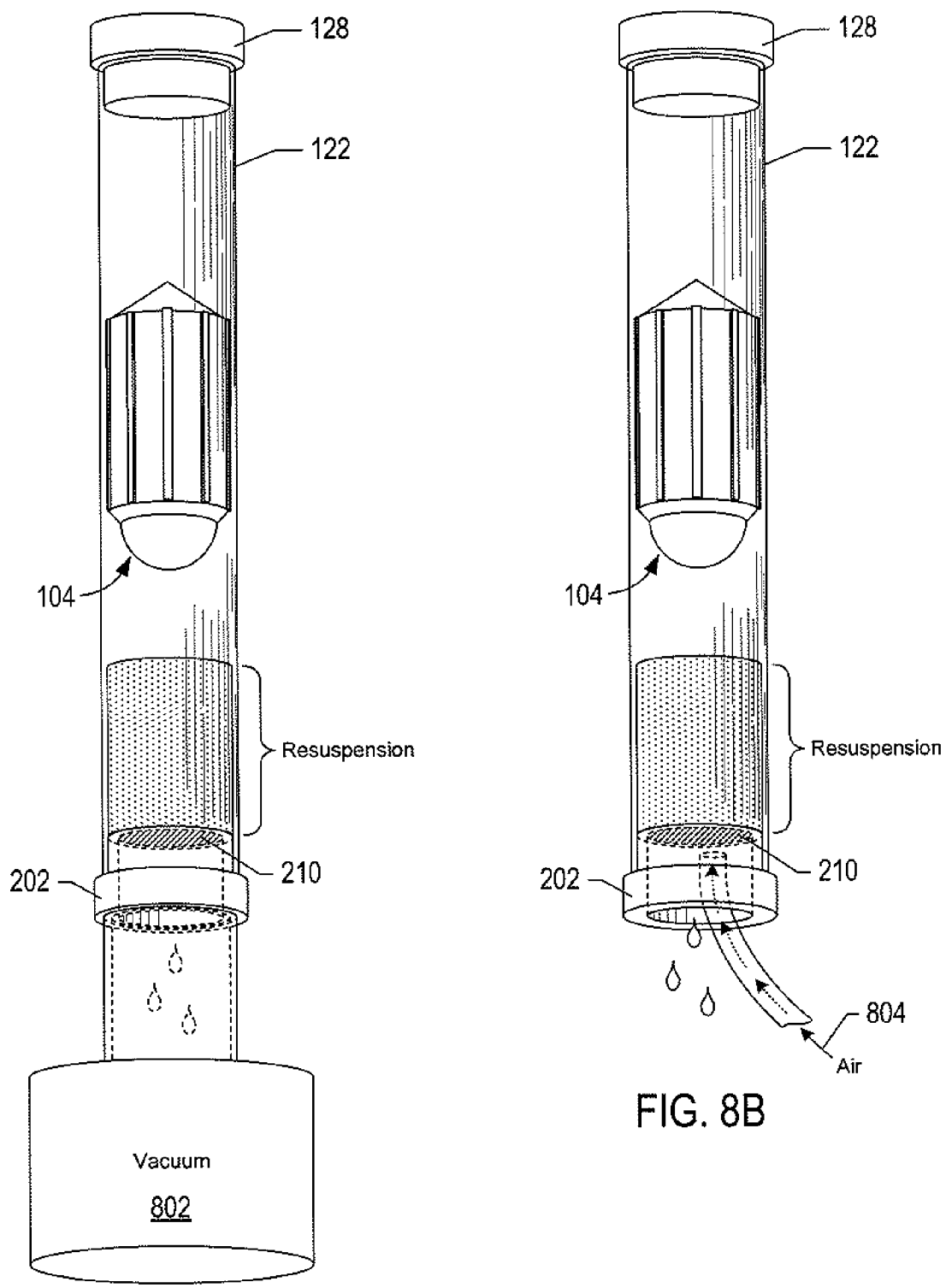
FIGS. 8A-8C show three examples of different devices that can be used to draw a resuspension fluid through a cap with a filter.
Figure 8C:
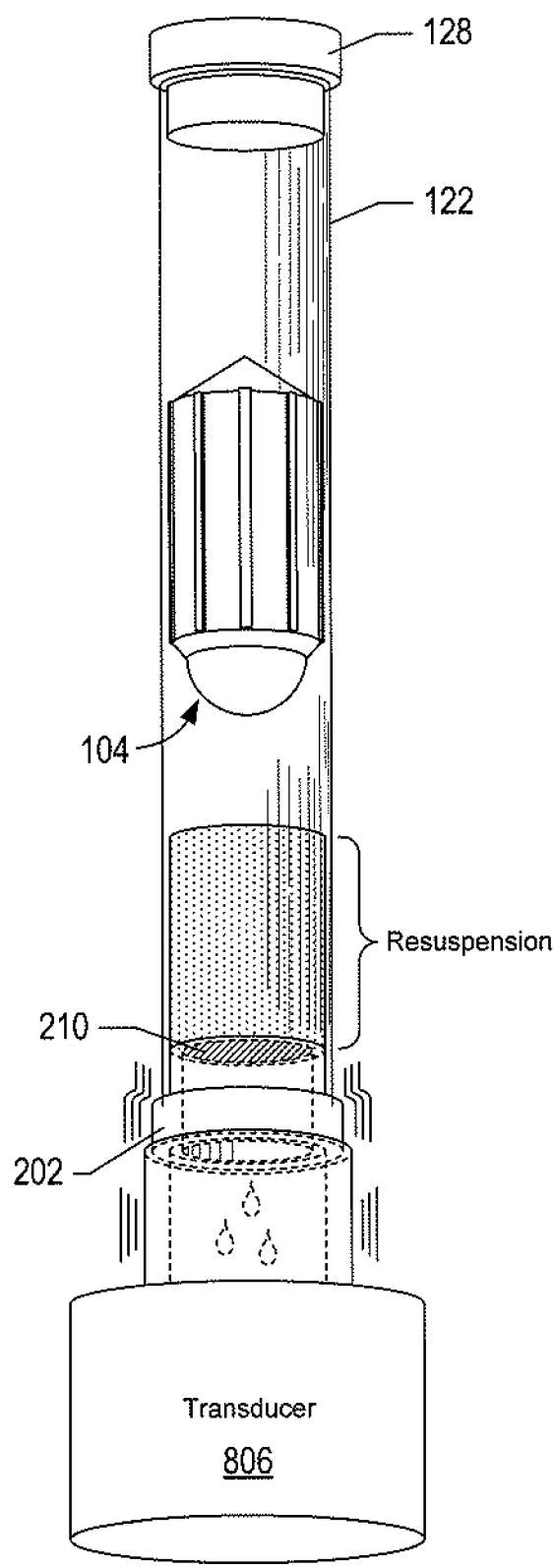

The resuspension fluid can also be drawn off using mechanical means. FIGS. 8A-8C show three examples of different devices that can be used to remove the resuspension fluid. In FIG. 8A, the inverted tube 122 is placed on a vacuum 802 that creates a small vacuum to draw the resuspension fluid through the filter 210. This pressurization cycle can be repeated until nearly all of the resuspension and buffy coat fluids have passed through the filter 210. In FIG. 8B, air pressure 804 can be applied through the filter 210 in the opposite direction of fluid flow in order to break up any wedges that may form. In FIG. 8C, a mechanical transducer 806 is used to vibrate the filter 210 or move the tube 122 in a swirling motion to prevent the formation of clogging wedges. The filter cap 202 is then removed and the CTCs deposited on the filter 210 are available for counting or molecular analysis.

Note that after the plasma 708 has been removed, as described above with reference to FIG. 7C, the buffy coat 704 can be isolated by pouring off the red blood cells 706 or suctioning the red blood cells 706 out with a pipette. Once the plasma 708 and the red blood cells 706 have been essentially removed, the portions of the buffy coat not attached to the surface of the float 104 can be washed into a container using a saline solution, enabling the remaining contents of the buffy coat to be further analyzed.

Embodiments are not limited to using the tube and float system 120. Alternatively, because the tube 102 of the tube and float system 100 is composed of a flexible material, the tube 102 can also be inserted into the system 710 with the needles 716 and 718 puncturing the closed end 108 of the tube 102. CTCs trapped between the float 104 and the tube 102 wall can then be collected on the filter 210 by inverting the tube 102 and pouring the resuspension fluid into the holes formed in the closed end 108.

Figure 9:
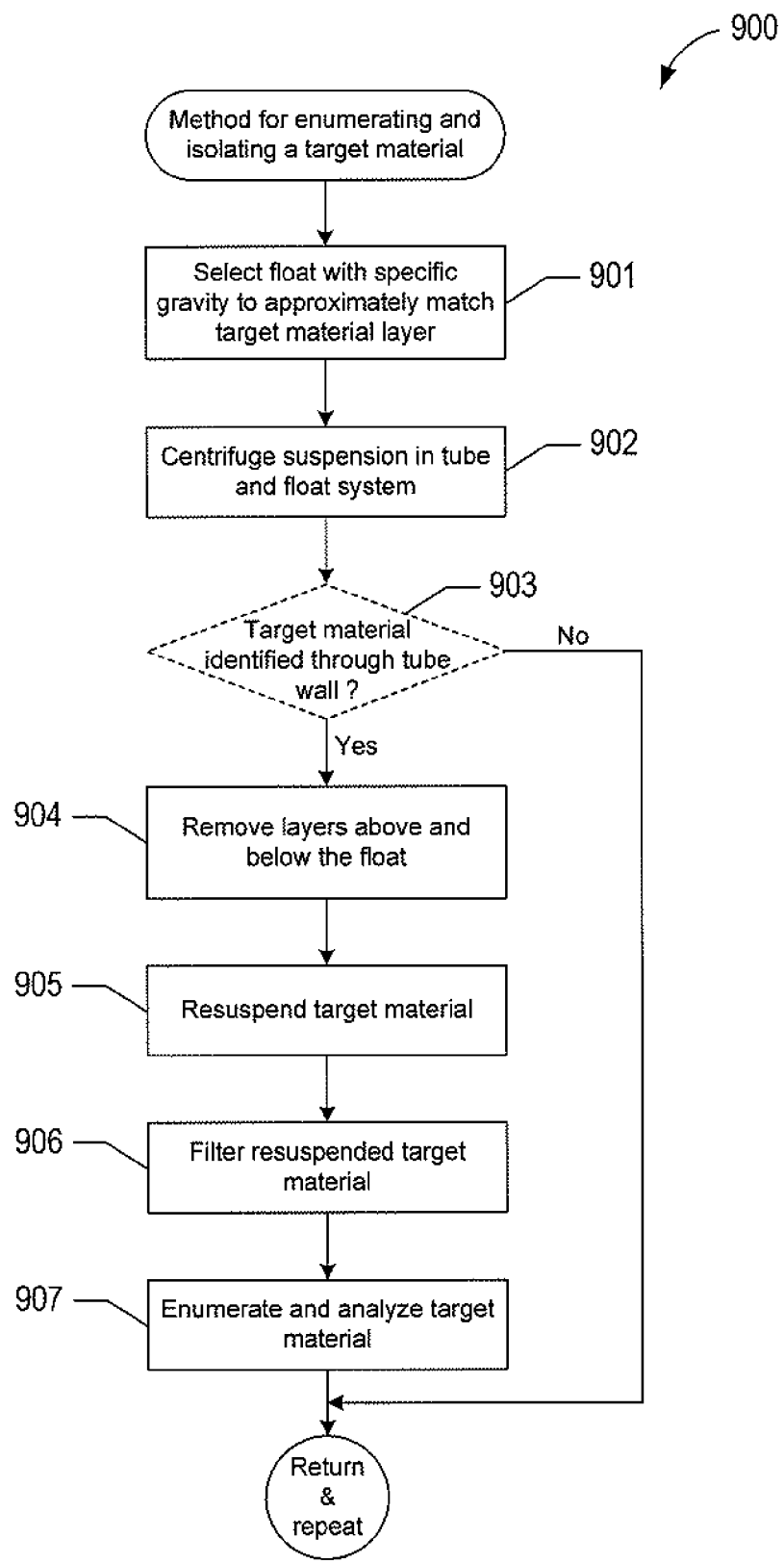
FIG. 9 shows a control-flow diagram summarizing a general method for isolating target materials of a suspension.

FIG. 9 shows a control-flow diagram that summarizes a method 900 of isolating a target material of a suspension. In block 901, a float with a specific gravity corresponding to the specific gravity of a layer containing the target material is selected, as described above with reference to FIG. 7A. In block 902, the float is inserted into the tube along with the suspension suspected of containing the target material and the tube, float and suspension are centrifuged in order to separate the particle components of the suspension according their specific gravities, as described above with reference to FIG. 7B. In block 903, when the target material is identified through the wall of the tube, the method proceeds to block 904. Otherwise, the method proceeds to block 908 where the method 900 is repeated for another suspension. Alternatively, block 903 is omitted and the method 900 proceeds directly from block 902 to block 904. In block 904, layers located above and below the float are removed, as described above with reference to FIG. 7C-7E. In block 905, a fluid is introduced to the tube to resuspend the target material within a resuspension followed by rocking or agitating the tube. In block 906, the resuspension is extracted through a filter in the cap of the tube to collect the target material on the filter. In block 907, the target material trapped on the filter is enumerated and can be analyzed.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Obviously, many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

The invention claimed is:

1. A method for harvesting at least one target material of a suspension, the method comprising:
   centrifuging the suspension in a tube and float system, wherein a layer suspected of containing the at least one target material is disposed between the outer surface of the float and inner wall of the tube;
   removing layers located above and below the float;
   introducing a solution to the tube to re-suspend the at least one target materials in a resuspension;
   draining the resuspension through a filter located in a cap covering an open end of the tube; and
   trapping the at least one target material against the filter.

2. The method of claim 1, further comprising applying a vacuum to draw the resuspension through the filter located in the cap.

3. The method of claim 1, further comprising applying air pressure to the filter to prevent wedges from forming on the filter.

4. The method of claim 1, further comprising agitating the filter to prevent wedges from forming on the filter.

5. The method of claim 1, further comprises counting the at least one target material trapped against the filter.

6. The method of claim 1, wherein draining the resuspension through the filter further comprises inverting the tube to gravity filter the resuspension.

7. The method of claim 1, wherein the suspension further comprises a whole blood sample.

8. The method of claim 1, wherein the at least one target material further comprises circulating tumor cells.

9. A system for harvesting at least one target material of a suspension, the system comprising:
   a tube having an open end for receiving a suspension suspected of containing the at least one target material;
   a float disposed within the tube and having a specific gravity to position the float at approximately the same level as a layer containing the at least one target material; and
   a cap including a filter that when placed on the open end traps the at least one target material when the target material suspended within a fluid is poured through the filter by inverting the tube.

10. The system of claim 9, further comprising a vacuum attached to the open end of the tube to draw the suspension through the filter located in the cap.

11. The system of claim 9, further comprising a transducer attached to the open end of the tube to agitate the filter to prevent wedges from forming on the filter.

12. The system of claim 9, wherein the cap including the filter further comprises a plug that seals the open end of the tube, the filter embedded within the plug.

13. The system of claim 9, wherein the tube and the cap including the filter further comprises the cap including a threaded plug, the filter embedded within the plug, and the tube inner wall near the tube open end threaded to receive a threaded plug of the cap.

14. The system of claim 9, wherein the cap including the filter further comprises an inner ring configured to form a snap-on sealing engagement with the open end of the tube.

15. The system of claim 9, wherein the tube and the cap including the filter further comprises the cap including a lid and a threaded portion, the filter embedded within the lid, and the tube outer wall near the tube open end threaded to receive the cap.

* * * * *